United States Patent [19]

Andriollo et al.

[11] Patent Number: 5,153,127
[45] Date of Patent: Oct. 6, 1992

[54] AB-011 ANTIBIOTICS AND PROCESS FOR PRODUCING THEM

[75] Inventors: Nunzio Andriollo, Bollate; Daniela Tolentino, Milan; Giorgio Cassani, Arluno; Giorgio Borgonovi, Milan; Marco Vincenti, Turin; Silvia Spera, Daverio; Luigi Mirenna, Milan; Giorgio Pirali, Saronno; Giovanni Confalonieri, Monza, all of Italy

[73] Assignee: Presidenza del Consiglio dei Ministri, Rome, Italy

[21] Appl. No.: 800,737

[22] Filed: Dec. 3, 1991

Related U.S. Application Data

[63] Continuation of Ser. No. 528,894, May 29, 1990, abandoned, which is a continuation of Ser. No. 366,550, Jun. 14, 1989, abandoned.

[30] Foreign Application Priority Data

Jun. 14, 1988 [IT] Italy .................... 20956 A/88

[51] Int. Cl.$^5$ ............................... C12P 1/06
[52] U.S. Cl. ..................... 435/169; 435/886; 435/253.5; 435/41; 435/128; 435/252.1; 435/105; 424/115; 424/116; 424/93 G

[58] Field of Search ........... 435/886, 253.5, 41, 435/128, 169, 252.1, 105; 424/115, 116, 93

[56] References Cited

U.S. PATENT DOCUMENTS

| 3,689,639 | 9/1972 | Bergy et al. | 435/886 |
| 4,397,950 | 8/1981 | Dolak et al. | 435/886 |
| 4,534,965 | 8/1985 | Brown et al. | 435/886 |
| 4,540,661 | 9/1985 | Hannon et al. | 435/886 |

OTHER PUBLICATIONS

Satomi et al., Chemical Abstracts, 98(1):2537c.
Ubukata et al., Chemical Abstracts, 104(21):182955m.

Primary Examiner—Ronald W. Griffin
Assistant Examiner—Pamela S. Webber
Attorney, Agent, or Firm—Morgan & Finnegan

[57] ABSTRACT

The AB-011 Antibiotics and the main components thereof: AB-011a and AB-011b, obtained by the controlled aerobial cultivation of Streptomyces s.p. NCIB 12629 in an aqueous nutrient cultivation medium. The AB-011 Antibiotics show a biological activity, and in particular an antifungal activity.

12 Claims, 10 Drawing Sheets

AB-011 ANTIBIOTICS AND PROCESS FOR PRODUCING THEM

This is a continuation of co-pending application Ser. No. 528,894, filed on May 29, 1990, now abandoned, which is a continuation of application Ser. No. 366,550, filed Jun. 14, 1989, abandoned.

DESCRIPTION OF THE INVENTION

1. Field of the Invention

The present invention relates to antibiotic substances arbitrarily denominated as "AB-011 Antibiotics" and to the main components thereof: AB-011a Antibiotic and AB-011b Antibiotic.

Furthermore, the present invention relates to the process for preparing them by the fermentation of Streptomyces SP. NCIB 12629, and to their use in the treatment of the infective diseases caused by microorganisms susceptible to them.

2. Background of the Invention

AB-011 Antibiotics are different from the other antibiotics known from the prior art.

The term "AB-011 Antibiotics" used herein indicates a mixture which comprises all of the components endowed with biological activity, for example of the antifungal type, produced by the fermentation of Streptomyces SP. NCIB 12629 under such conditions as will be specified in the following. These active components comprise, but are not limited to, those designated as AB-011a and AB-011b Antibiotics, which were isolated from the mixture.

Those skilled in the art of fermentation will be well aware that the number and the mutual ratios of the components which form the AB-011 Antibiotics may vary as a function of the fermentation conditions, and of the bacterial strain used.

One should furthermore understand that the present invention is not limited to the use of Streptomyces SP. NCIB 12629, but comprises also the use of either natural or artificial mutants and variants of the above-said microorganisms, on condition that they produce the AB-011 Antibiotics.

DETAILED DESCRIPTION OF THE INVENTION

Therefore, the objects of the present invention are the AB-011 Antibiotics obtainable by the controlled cultivation, under aerobic conditions, of Streptomyces SP. NCIB 12629, or of an equivalent mutant thereof, in an aqueous nutrient cultivation medium containing sources of carbon, nitrogen and inorganic salts, and the subsequent separation of said antibiotics and of the main components thereof: AB-011a and AB-011b Antibiotics.

PHYSICAL-CHEMICAL CHARACTERISTICS OF AB-011a Antibiotic

Figure 1:
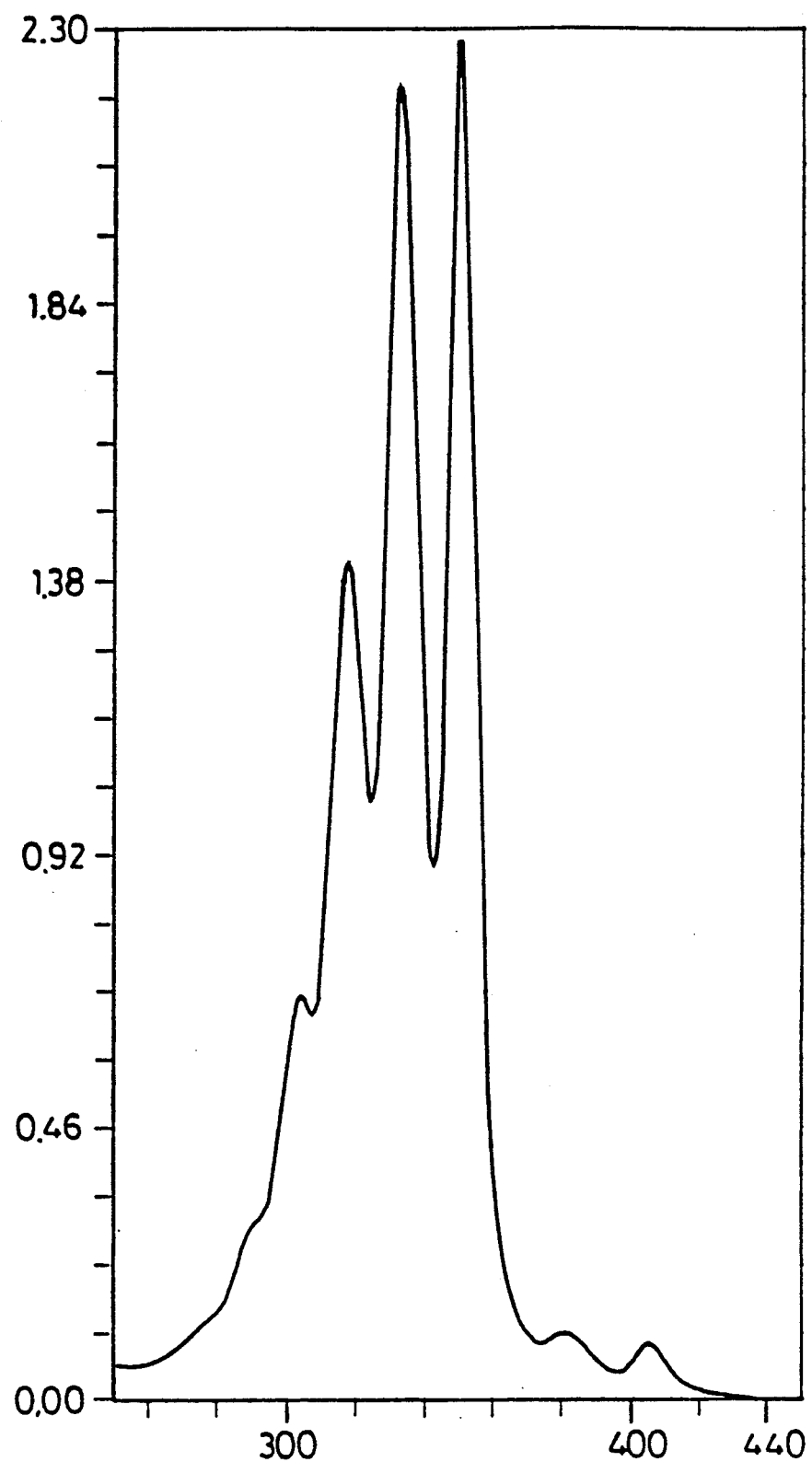
FIGS. 1-10 show physical-chemical characteristics of the present antibiotic.
Figure 2:
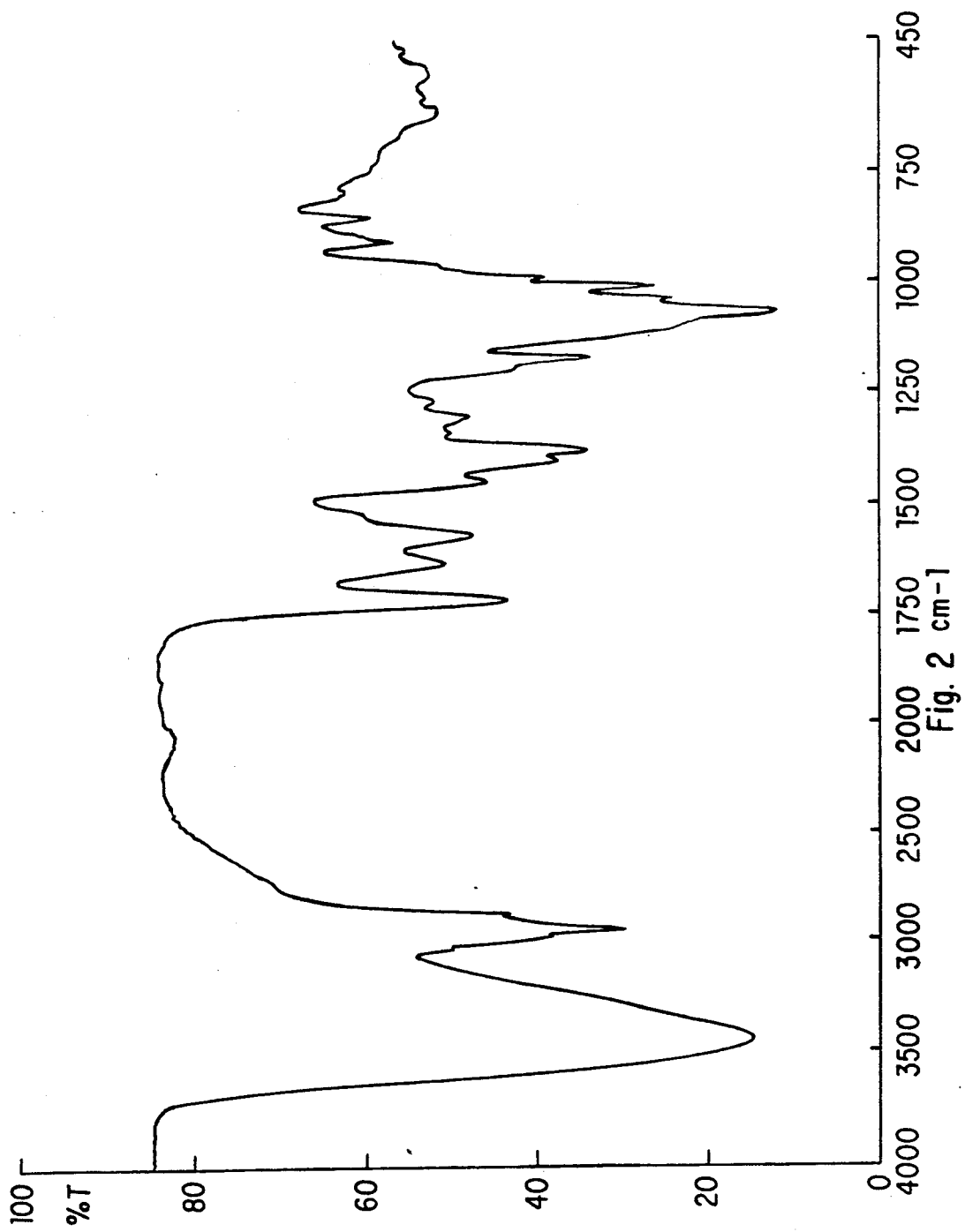
Figure 3:
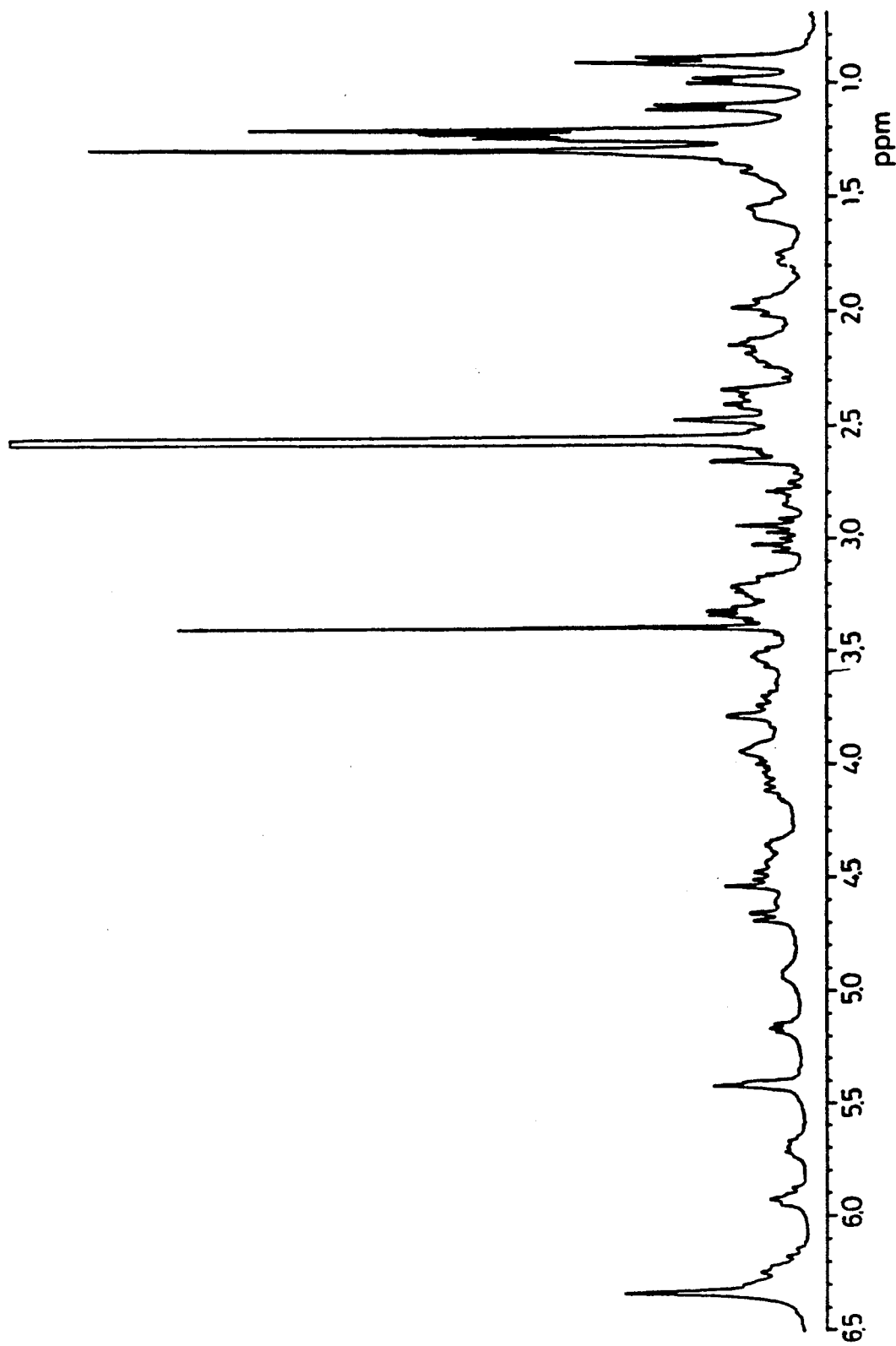

AB-011a Antibiotic, a component of AB-011 Antibiotics, is a powder of light yellow color, characterized by:

(a) a good solubility in dimethylsulfoxide and in (1:1 V/V) ethanol/water or (1:1 V/V) methanol/water blends [V/V=volume/volume], poor solubility in water, rather good solubility in ethanol and methanol;

(b) an approximate elemental analysis, determined on a sample left standing under vacuum at 40° C. for 2 hours, expressed as % values:
carbon: 58.86;
hydrogen: 7.64; and
nitrogen: 1.11; and containing neither sulfur nor phosphorous;

(c) a molecular weight of about 1,197.65 as computed from FAB-MS spectrum, which shows a peak at 1,196.65, corresponding to (M-H), under the following operating conditions:
Negative ions, FAB, Xe at 9.5 kV;
Matrix:glycerol;
Finnigan Mat 8424;

(d) the U.V. absorption spectrum shown in FIG. 1 of the accompanying drawings, revealing an absorbance maximum of 2.269 at 350.4 nm; 2.197 at 332.6 nm; 1.403 at 317.3 nm; 0.679 at 303.3 nm; 0.118 at 381.1 nm; 0.097 at 405.6 nm, at a concentration of 0.029 mg/ml of methanol;

(e) the I.R. absorption spectrum in KBr pellet is shown in FIG. 2 of the accompanying drawings, and shows the following absorption maxima $cm^{-1}$):
3421, 2960, 2930, 2855, 2035, 1718, 1634, 1570, 1448, 1403, 1383, 1340, 1302, 1268, 1168, 1063, 1036, 1009, 989, 906, 848, 794, 575, 526, 473;

(f) the N.M.R. spectrum of $^1H$ is shown in FIG. 3, and reveals signals recorded by means of a BRUKER AM 300 MHz spectrometer in hexa-deutero-dimethylsulfoxide (DMSOd6). The chemical shifts were indirectly referred to $\delta TMS = 0.00$ ppm ($\delta TMS$), using as the internal reference the central peak of hexa-deutero-dimethylsulfoxide taken at $\delta TMS = 2.56$ ppm:

$\delta TMS$ (ppm): 6.45–6.10* (m, 8H); 5.92 (m, 1H); 5.69 (m, 1H); 5.41 (m, 2H); 5.15 (m, 1H); 4.92 (m, 1H), 4.77–4.22 (m, 6H); 4.22–3.45* (m, 8–10H); 3.37–3.07(m, 6–7H); 3.02 (t, 1H); 2.93 (t, 1H); 2.88–2.72* (m, 3H); 2.45–2.27* (m, 3–4H); 2.27–2.05* (m, 3H); 2.05–1.85* (m, 3H); 1.85–1.66* (m, 1H); 1.66–1.15* (m, 30–33H); 1.10 (d, 3H); 0.99 (d, 3H); 0.90 (m, 6H). (The number of hydrogen atoms assigned to the signals marked with an asterisk is indicative only, in that it may be affected by error.)

Figure 4:
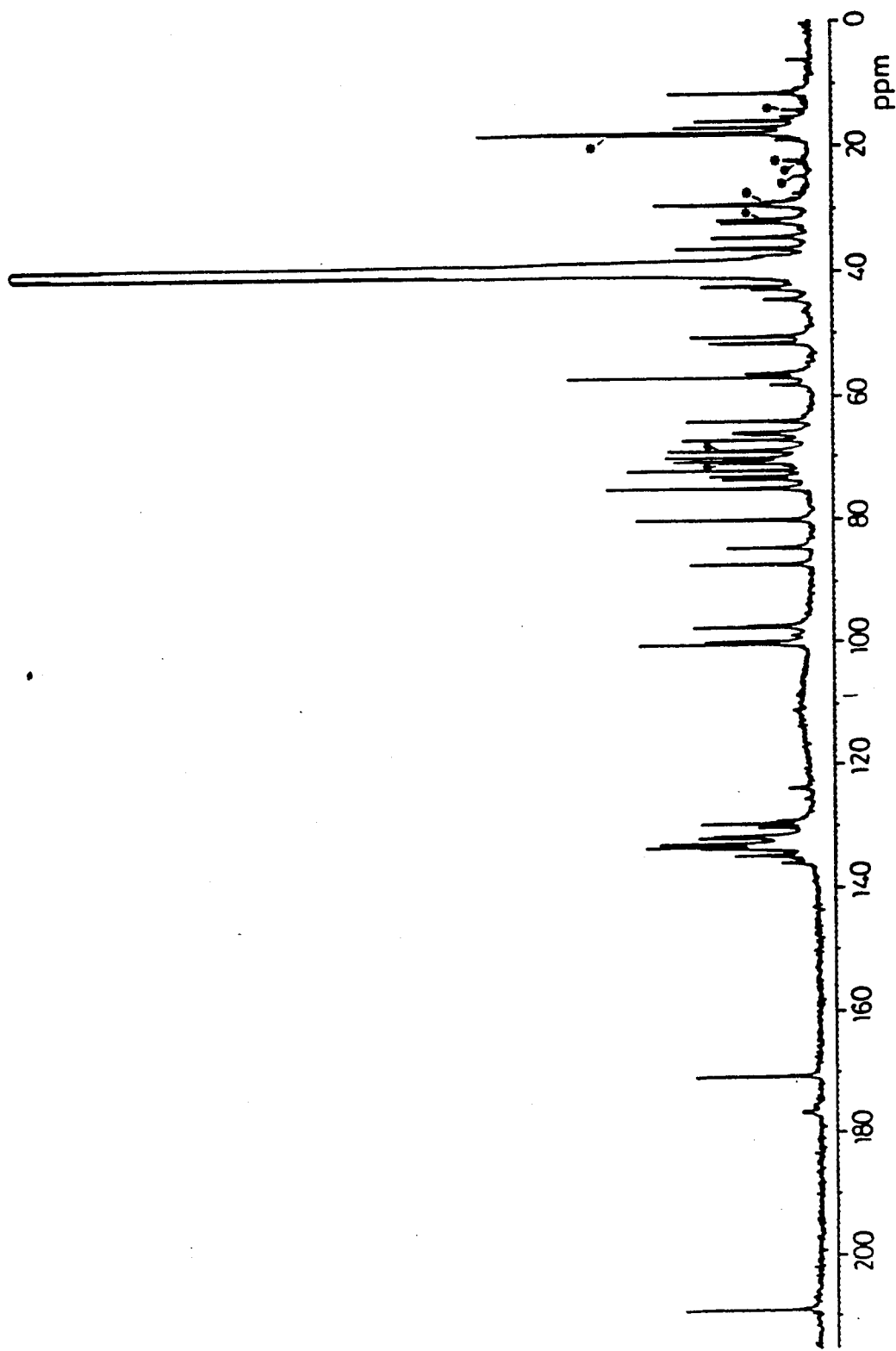

(g) the N.M.R. spectrum of $^{13}C$ is reported in FIG. 4 and shows signals recorded by means of BRUKER AM 300 MHz spectrometer in hexa-deutero-dimethylsulfoxide (DMSOd6). The chemical shifts were indirectly referred to $\delta TMS = 0.00$ ppm ($\delta TMS$), using as the internal reference the central peak of hexa-deutero-dimethylsulfoxide taken at $\delta TMS = 39.85$ ppm.

The data relevant to the multiplicity of the signals were obtained by means of DEPT tests at 45, 90 and 135.

$\delta TMS$ (ppm): 208.6 (s); 176.3 (s); 170.3 (s); 135.8 (d); 134.6 (d); 133.5 (d); 133.2 (d); 132.9 (d); 132.7 (d); 131.7 (d); 131.4 (d); 130.0 (d); 129.5 (d); 100.3 (d); 99.8 (d); 97.4 (s); 97.3 (d); 87.1 (d); 84.4 (d); 79.9 (d); 75.0 (d); 73.5 (d); 73.1 (d); 72.1 (d); 70.7 (d); 70.0 (d); 69.0 (d); 67.1 (d); 66.1 (d); 65.9 (d); 64.0 (d); 58.1 (d); 56.9 (q); 56.3 (d); 51.6 (t); 50.5 (t); 44.7 (t); 43.0 (t); 42.5 (t); 39.7 (d); 39.4 (d);

39.0 (t); 37.5 (t); 36.3 (t); 34.4 (t); 32.1 (t); 31.7 (t); 29.3 (t); 18.0 (q); 17.9 (q); 17.1 (q); 16.0 (q); 11.5 (q).

Furthermore some peak—marked with an asterisk in FIG. 4—were recorded, whose attribution to AB-011a Antibiotic is uncertain, in that they are of variable intensity according to the origin of the analyzed sample: said peaks could be originated by products of decomposition of the same product: the following is a list of said peaks: δTMS (ppm): 70.9 (d); 68.9 (d); 31.5 (t); 29.0 (t); 28.8 (t); 28.3 (t); 24.7 (t); 22.8 (q); 22.3 (t); 18.0 (t); 14.2 (q).

(h)
the retention coefficients in thin-layer chromatography with a run of the eluent of 15 cm, on silica slabs Kieselgel 60 F 254 (Merck-Schuchardt), and on reverse-phase silica slabs RP-18 F 254 (Merck-Schuchardt) in the following eluent systems and compared to AB-011b Antibiotic:

A eluent: methanol:25 mM monobasic potassium phosphate +7 mM tetramethyl-ammonium chloride in water (8:2);

B eluent: methanol:acetonitrile:25 mM monobasic potassium phosphate +7 mM tetramethyl-ammonium chloride in water (4:4:2);

C eluent: methanol:10 mM dibasic ammonium phosphate adjusted at pH 7.5 with phosphoric acid, in water (8:2);

D eluent: methanol:acetonitrile 10 mM dibasic ammonium phosphate adjusted at pH 7.5 with phosphoric acid, in water (4:4:2);

E eluent: ethanol:dioxane:aqueous solution of ammonia at 30% : water (8:1:1:1);

F eluent: methylene chloride:methanol (17:3);

| Slab | Eluent | $R_f$(AB-011a) | $R_f$(AB-011b) |
|---|---|---|---|
| RP-18 | A | 0.29 | 0.22 |
| RP-18 | B | 0.44 | 0.35 |
| RP-18 | C | 0.13 | 0.08 |
| RP-18 | D | 0.27 | 0.20 |
| Silica | E | 0.25 | 0.32 |
| Silica | F | 0.0 | 0.0 |

Visualization:
A. Florescence in U.V. light (366 nm);
B. Anisaldehyde (T-27 reactant) -- Thin Layer Chromatography -- page 205
C. o-Aminophenol (T-11 reactant) -- Thin Layer Chromatography -- page 201.
Author: Justus G. Kirchner - 2nd Ed. Publisher: John Wiley & Sons.

(i) Retention time ($R_t$) of about 7 minutes when analyzed on reverse-phase HPLC column under the following conditions:
Column: Hibar LichroCART (Li-Chrosorb (RP-18 (7 microns) 250×4.0 mm (Merck, Darmstadt, F.R. of Germany);
Forecolumn: Guard Pak RCSS C 18 (Millipore Waters);
Eluent: methanol:acetonitrile:25 mM monobasic potassium phosphate+7 mM tetramethyl-ammonium chloride in water (4:4:2);
Flowrate: 0.8 ml/minute;
Detector: U.V. at 333 nm;
Temperature: 40° C.; Under the same conditions AB-011b Antibiotic is eluted after about 9 minutes.

Figure 5:
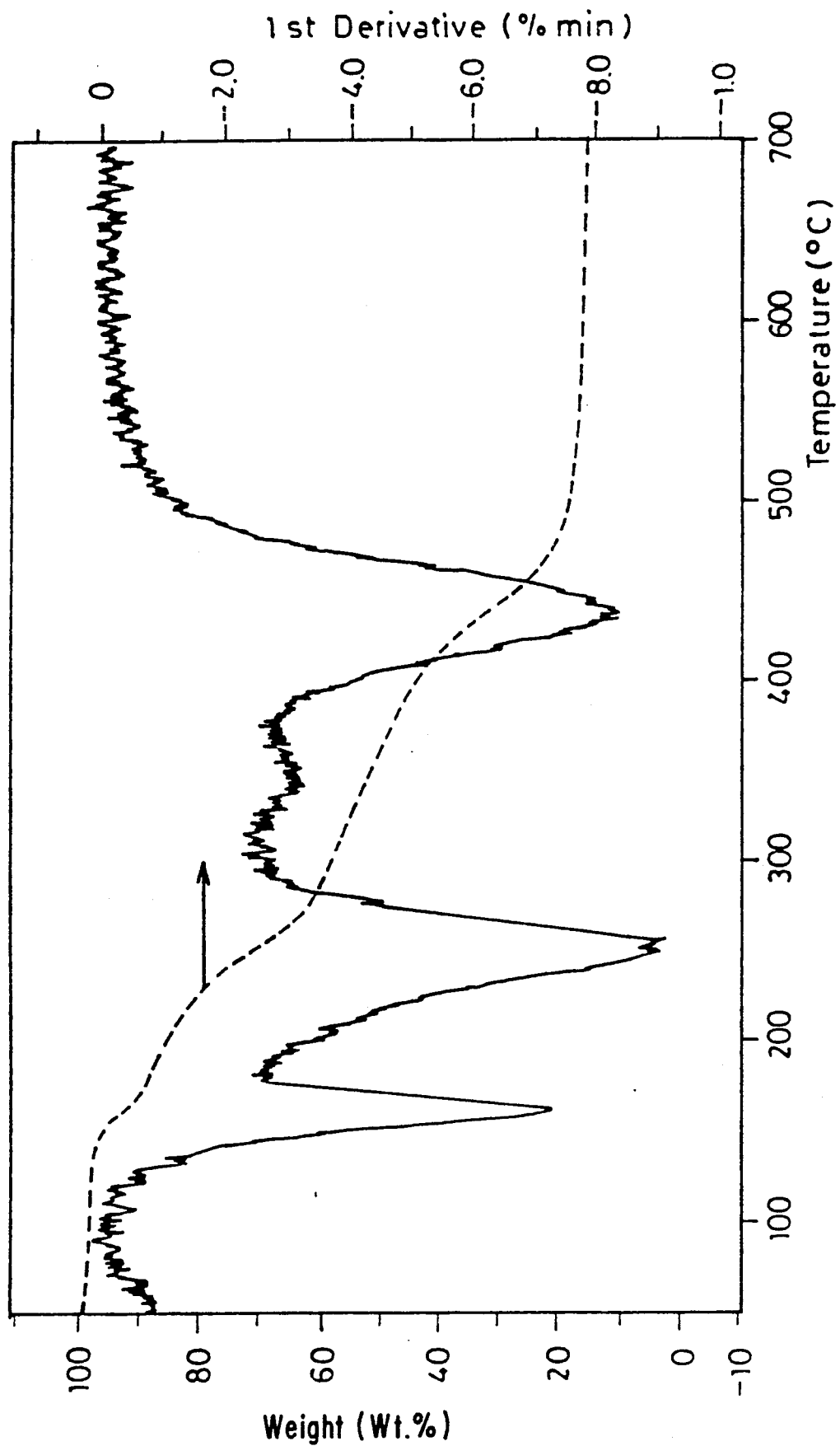

(j) The thermogravimetric analysis carried out under nitrogen, with a temperature increase rate of 20° C./minute within the temperature range of from 30° C. up to 700° C. on a PERKIN-ELMER 7 SERIES Thermal Analysis System, shows the trend reported in FIG. 5, in which on the abscissa the temperature is reported as °C., and on the ordinate the percent weight loss. In the same FIG. 5, the first derivative of the curve is also reported.

Physical-Chemical Characteristics of AB-011b Antibiotic

Figure 6:
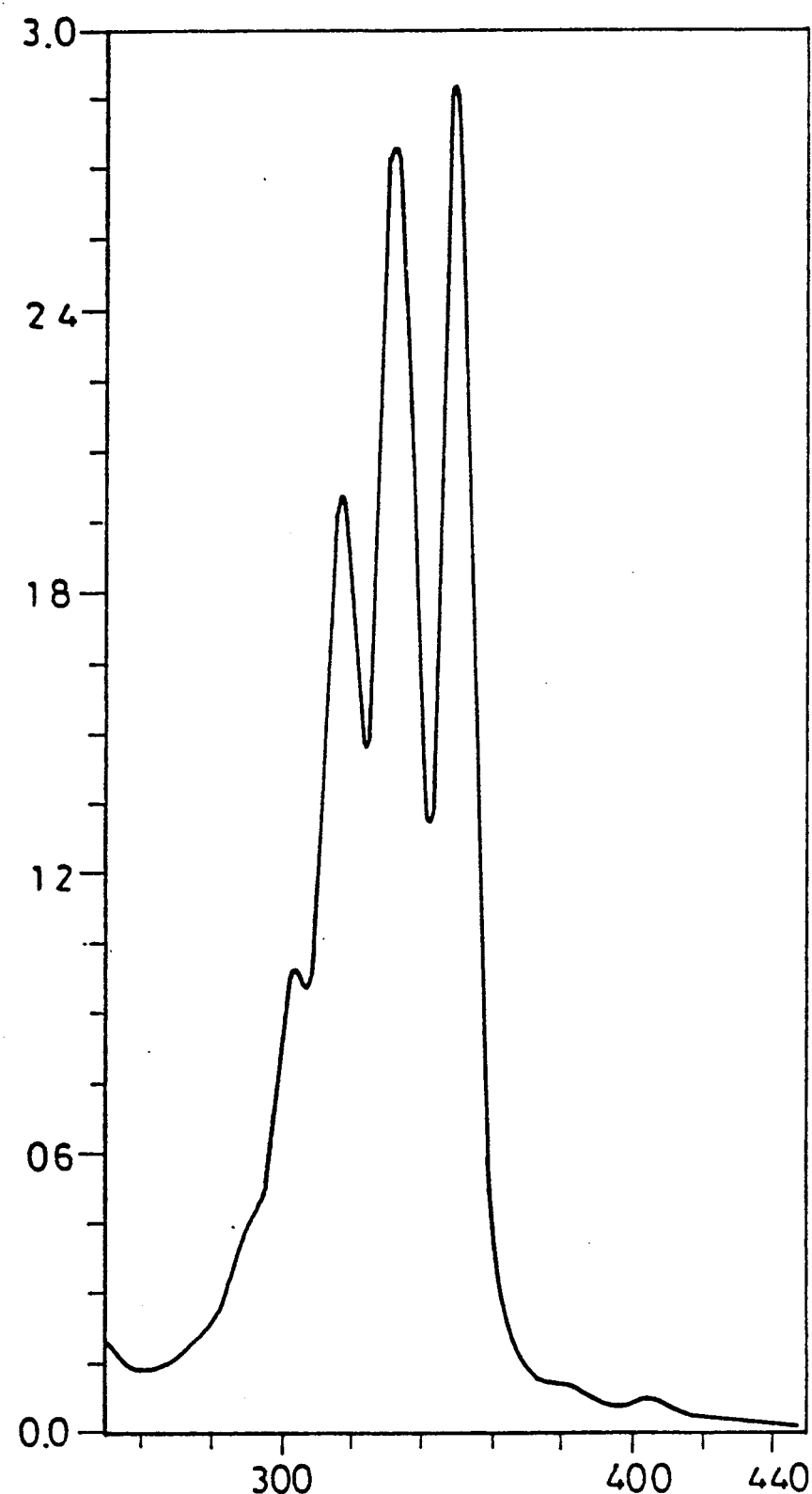
Figure 7:
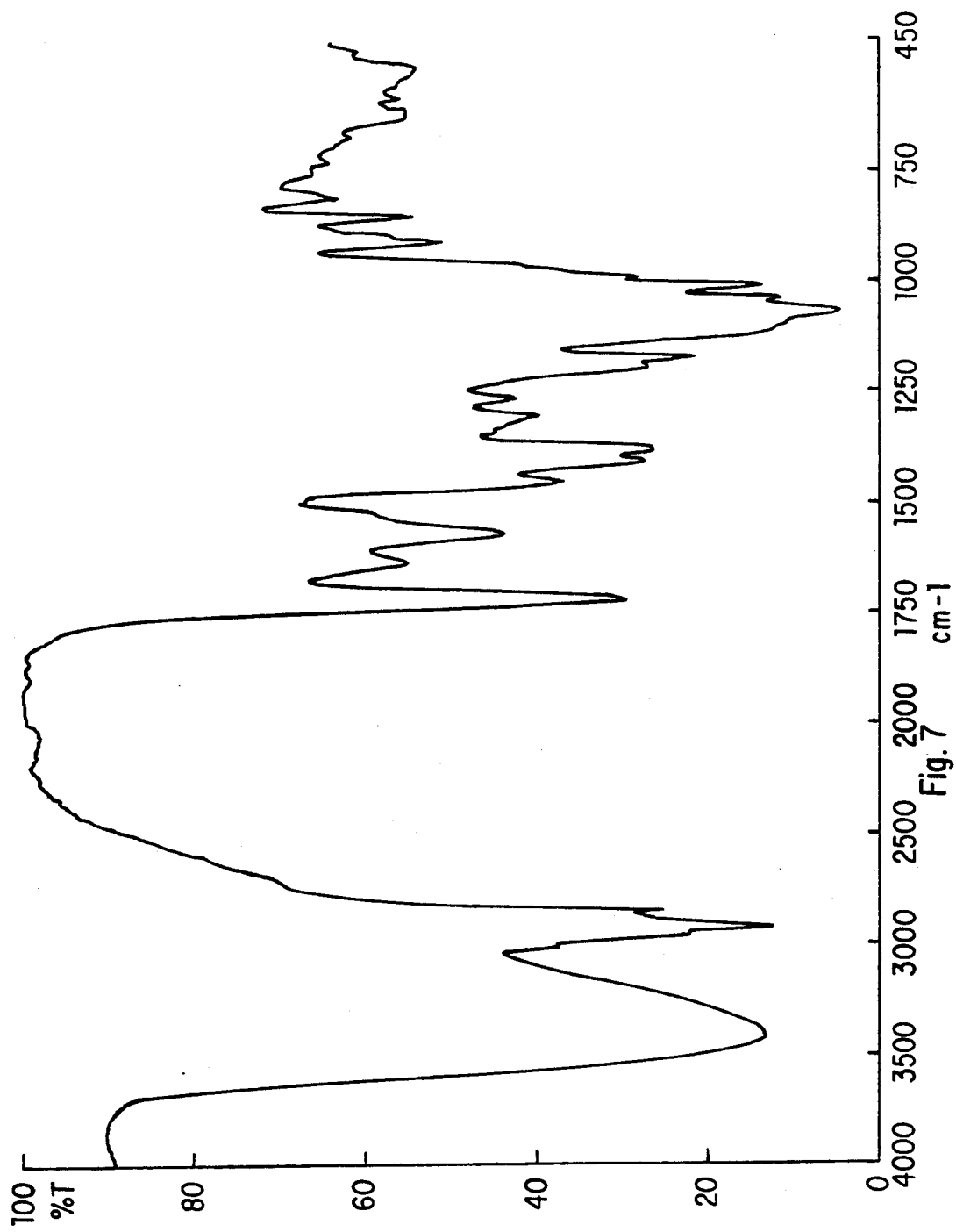
Figure 8:
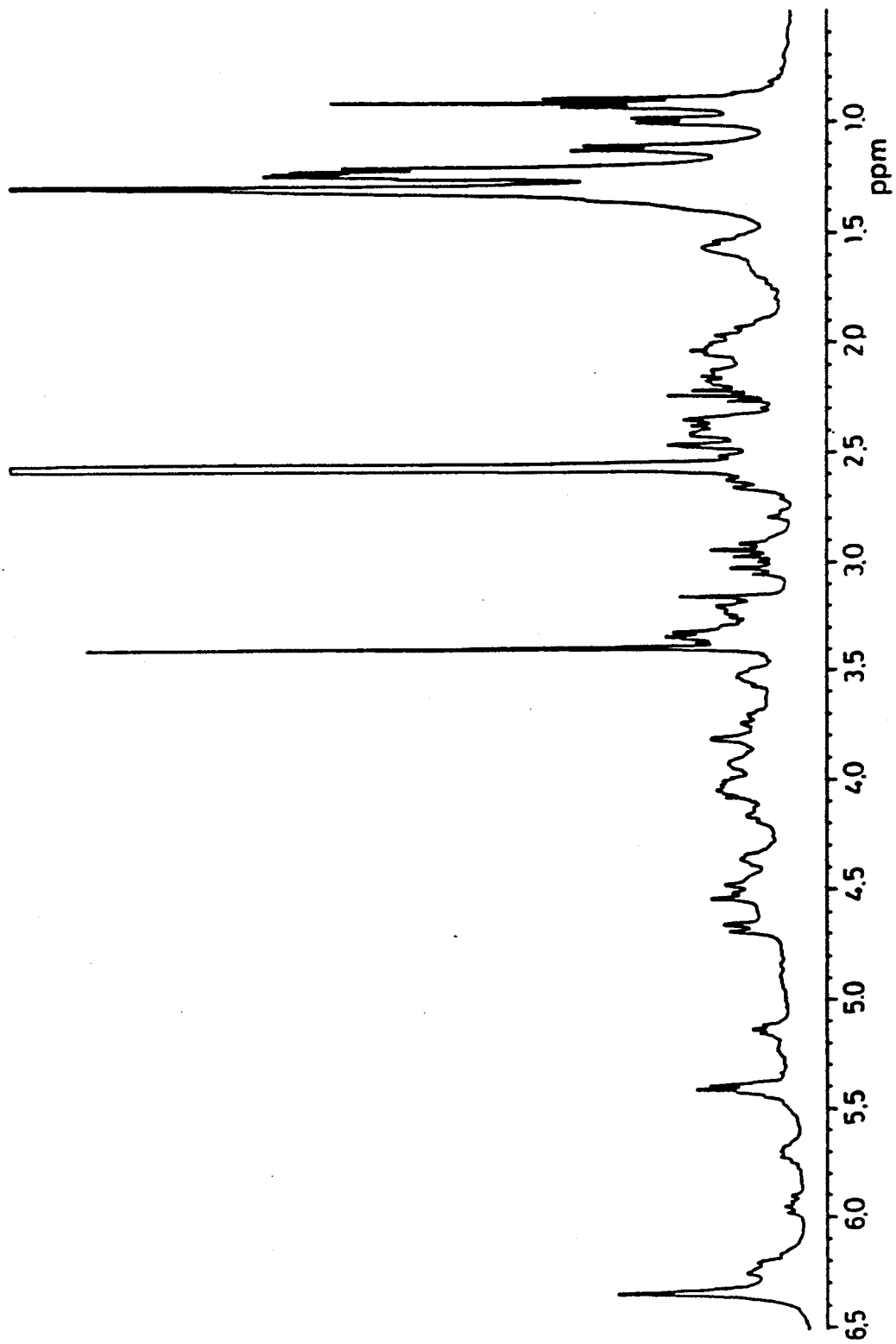

AB-011b Antibiotic, a component of AB-011 Antibiotics, is a powder of deep yellow color, characterized by:

(a) the U.V. absorption spectrum shown in FIG. 6 of the accompanying drawings. This FIG. 6 shows an absorbance maximum of 2.872 at 349.9 nm; 2.747 at 332.4 nm; 1.999 at 316.9 nm; 0.987 at 303.3 nm; at a concentration of 0.04 mg/ml of methanol;

(b) an approximate elemental analysis, determined on a sample left standing under vacuum at 40° C. for 2 hours, expressed as % values:
carbon: 58.51;
hydrogen: 8.14;
nitrogen: 1.03;
and containing neither sulfur nor phosphorous;

(c) the I.R. absorption spectrum in KBr pellet is reported in FIG. 7 of the accompanying drawings, and shows the following absorption maxima $cm^{-1}$):
3415, 2926, 2855, 2060, 1721, 1634, 1568, 1450, 1406, 1383, 1302, 1264, 1190, 1168, 1063, 1036, 1007, 988, 906, 847, 804, 722, 664, 618, 576, 509, 471, 446;

(d) a molecular weight of about 1,181 as computed from FAB-MS spectrum, which shows a peak at 1,180, corresponding to (M-H) , under the following operating conditions:
Negative ions, FAB, Xe at 9.5 kV;
Matrix: glycerol;
Finnigan Mat 8424;

(e) the N.M.R. spectrum of $^1$H is reported in FIG. 8 of the accompanying drawings and shows signals recorded by means of a BRUKER AM 300 MHz spectrometer in hexa-deutero-dimethylsulfoxide (DMSOd6).
The chemical shifts were indirectly referred to TMS=0.00 ppm (δTMS), using as the internal reference the central peak of hexa-deutero-dimethylsulfoxide taken at δTMS=2.56 ppm:
δTMS (ppm): 6.45–6.05* (m, 8H), 5.93 (m, 1H); 5.70 (m, 1H); 5.40 (m, 2H); 5.13 (m, 1H); 4.73–4.30 (m, 6H); 4.27–3.45* (m, 8–9H); 3.37–3.09* (m, 6–7H); 3.02 (t, 1H); 2.94 (t, 1H); 2.75–2.60* (m, 1H); 2.44–2.28* (m, 3H); 2.28–1.81 (m, 7–8H); 1.81–1.47* (m, 5H); 1.47–1.16* (m, 30–33H); 1.11 (d, 3H); 0.99 (d, 3H); 0.91 (m, 6H). (The number of hydrogen atoms assigned to the signals marked with an asterisk is indicative only, in that it may be affected by error.)

Figure 9:
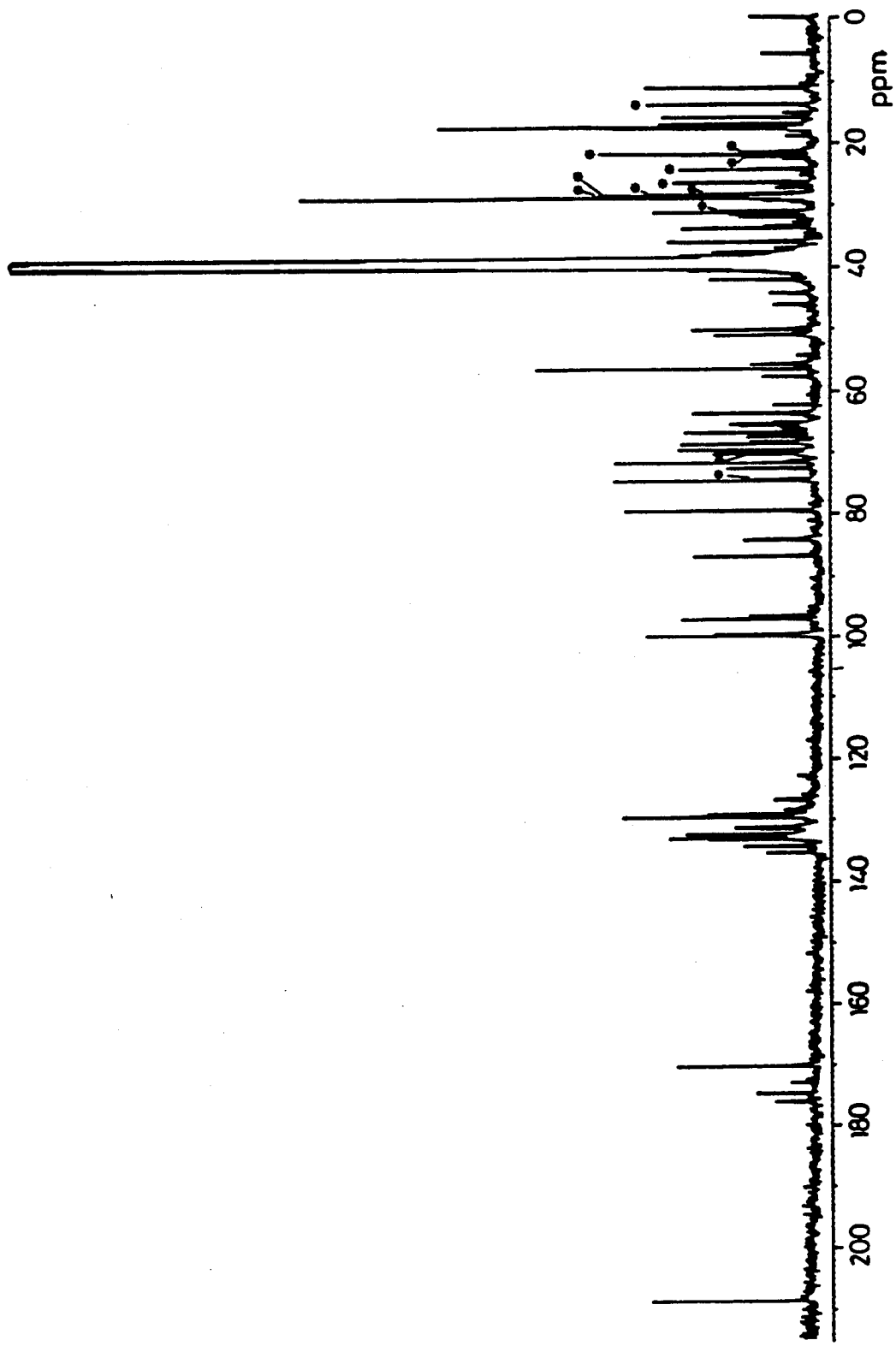

(f)
the N.M.R. spectrum of $^{13}$C is reported in FIG. 9 of the accompanying drawings, and shows signals recorded by means of a BRUKER AM 300 MHz spectrometer in hexa-deutero-dimethylsulfoxide (DMSOd6).
The chemical shifts were indirectly referred to TMS=0.00 ppm (δTMS), using as the internal reference the central peak of hexa-deutero-dimethylsulfoxide taken at δTMS 39.85 pp.

The data relevant to the multiplicity of the signals were obtained by means of DEPT tests at 45, 90 and 135.

δTMS (ppm): 208.7 (s); 176.3 (s); 174.9 (s); 170.4 (s); 135.7 (d); 134.7 (d); 133.5 (d); 133.3 (d); 132.9 (d); 132.7 (d); 131.7 (d); 131.5 (d); 130.0 (d); 129.5 (d); 100.3 (d); 100.0 (d); 97.4 (s); 96.9 (d); 87.2 (d); 84.5 (d); 80.0 (d); 75.1 (d); 74.9 (d); 73.1 (d); 72.2 (d); 70.7 (d); 70.0 (d); 69.0 (d); 68.5 (d); 67.8 (d); 67.1 (d); 65.9 (d); 65.7 (d); 63.9 (d); 58.1 (d); 56.9 (q); 56.2 (d); 51.5 (t); 50.7 (t); 46.5 (t); 44.7 (t); 42.5 (t); 39.1 (t); 38.5 (t); 38.0 (t); 36.3 (t); 34.1 (t); 32.3 (t); 31.8 (t); 31.6 (t); 29.3 (t); 18.1 (q); 18.0 (q); 17.9 (q); 17.4 (q); 16.3 (q); 11.6 (q).

Figure 10:
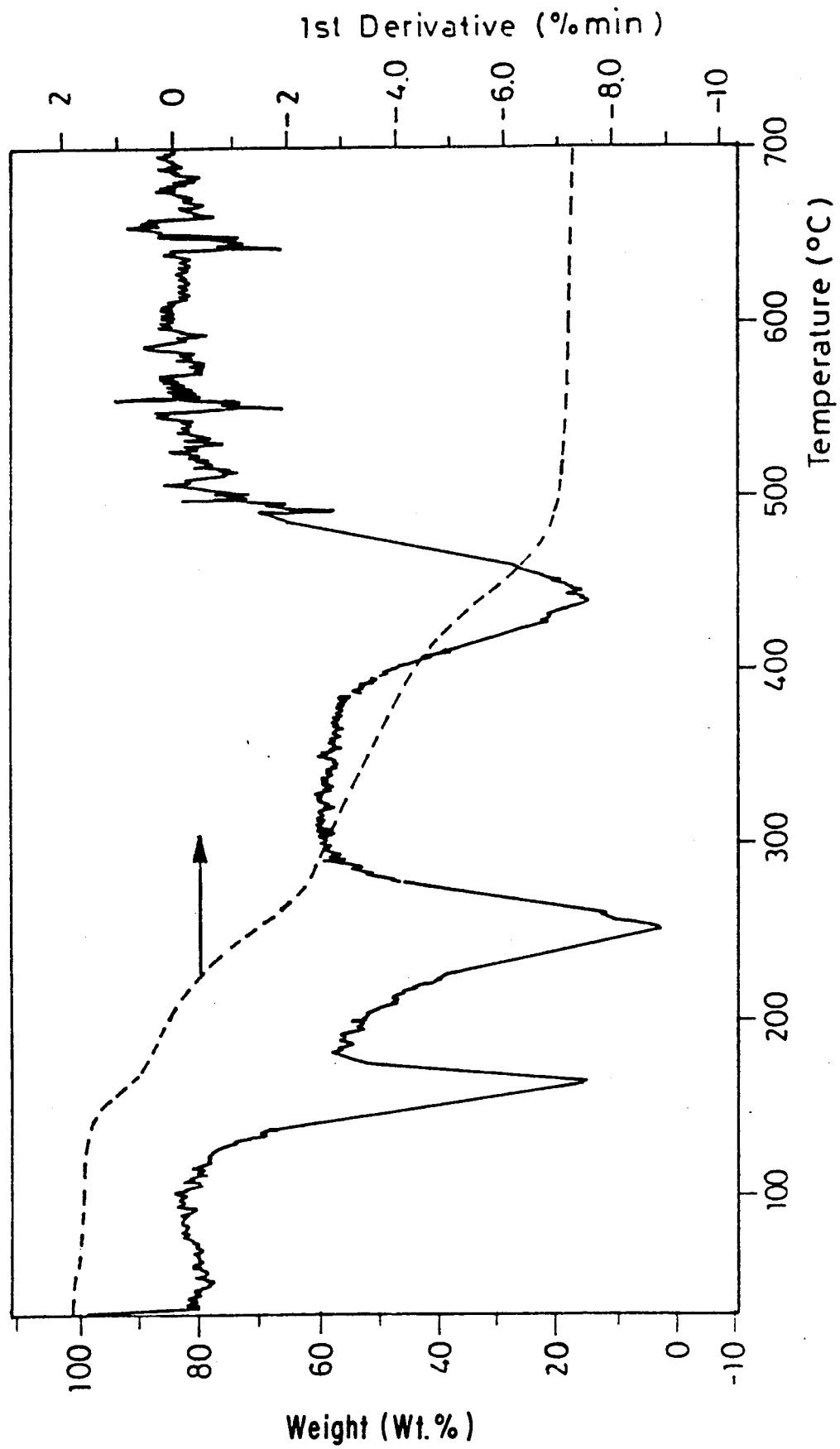

Furthermore, some peaks—marked with an asterisk in FIG. 9—were recorded whose attribution to AB-11b Antibiotic is uncertain, in that they are of variable intensity according to the origin of the analyzed sample: said peaks could originate from products of decomposition of the same product: the following is a list of said peaks:

δTMS (ppm): 74.9 (d); 70.5 (d); 31.4 (t); 29.0 (t); 28.9 (t); 28.8 (t); 28.6 (t); 26.9 (t); 24.8 (t); 22.8 (q); 22.4 (t); 22.0 (t); 14.3 (q);

(g) the thermogravimetric analysis carried out under nitrogen, with a temperature increase rate of 20° C./minute within the temperature range of from 30° C. up to 700° C. on a PERKIN-ELMER 7 SERIES Thermal Analysis System, shows the trend reported in FIG. 10, in which on the abscissa the temperature is reported as °C., and on the ordinate the percent weight loss. In the same FIG. 10 the first derivative of the curve is also reported.

(h) the retention coefficients ($R_f$) in thin-layer chromatography and the retention times ($R_t$) on reverse-phase HPLC column are respectively reported under the (h) and (i) paragraphs of the above description of the physical-chemical characteristics of AB-011a Antibiotic.

Morphology and cultural characteristics of microorganism Streptomyces SP. NCIB12629

The microorganism was isolated from a sample of soil collected at Varzo (Novara, Italy) catalogued under the conventional name of SD18.

A culture of this microorganism was filed on Jan. 22, 1988, in compliance with the Treaty of Bucharest, with the National Collection of Industrial Bacteria (c/o the National Collection of Industrial and Marine Bacteria Ltd., Torry Research Station, P.O. Box 31, 135 Abby Road, Aberdeen AB-98 DG, Scotland, United Kingdom), where it was given the access name of NICB 12629.

The morphologic characteristics of the strain are reported below in Table A (the names of the culture media are those as reported by the International Streptomyces Program).

In Table B below, some characteristics of this strain are reported:

In Table C below, the growth of the strain on some organic substances as the only source of carbon is reported:

TABLE A

| ISP Code | Culture Medium | Description |
|---|---|---|
| M2 | Malt Extract Agar | High, rough colonies with a base mycelium of light color; the spores are plentiful and are of light yellow color. |
| M3 | Oat Meal Agar | Low colonies, "radiated" base mycelium of light color; white spores. |
| M4 | Starch Agar | Scarce growth, white spores. |
| M5 | Glycerol Asparagine Agar | Scarce growth, white spores. |
| M6 | Peptone Iron Agar | Not very high colonies, light-colored mycelium, white spores. |
| M7 | Tyrosine Agar | High colonies, base mycelium of brown spores, gray spores; formation of an intense melanoid pigment. |
| — | Nutrient Agar | Large, high, rough colonies, with yellow spores. |
| — | Dextrose Potato Agar | High colony, base mycelium of orange color, spores of light gray color; intense, diffused melanoid pigment. |

TABLE B[2]

| Characteristics | Response |
|---|---|
| Resistance to NaCl (7%) | Positive |
| Resistance to phenol (0.1%) | Positive |
| Resistance to Rifampicin (50 μg/ml) | Negative |
| Growth at 45° C. | Negative |
| Growth at 4° C. | Positive |
| Nitrate reduction | Positive (nitrite formation) |
| Lecithin degradation | Positive |
| Allantoin degradation | Negative |
| Pectin degradation | Negative |

[2](Tests carried out according to the method described by S. T. Williams, M. Goodfellow, E. M. H. Wellington, J. C. Vickers, G. Alderson, P. H. A. Sneath, M. J. Sackin, A. M. Mortimer; Journal of General Microbiology, 1983, 129, 1815–1830).

TABLE C

| Compound | Growth |
|---|---|
| 2-keto-gluconate | negative |
| adonitol | negative |
| arabinose | negative |
| cellobiose | negative |
| fructose | positive |
| galactose | negative |
| glycerol | positive |
| glucose | positive |
| inositol | positive |
| lactose | negative |
| maltose | negative |
| mannitol | positive |
| melezitose | negative |
| methyl-D-glucoside | negative |
| N-acetyl-D-glucosamine | positive |
| raffinose | negative |
| rhamnose | positive |
| saccharose | negative |
| sorbitol | negative |
| trehalose | positive |
| xylitol | negative |
| xylose | negative |

The analysis of the cellular wall of SD18 strain carried out according to the method described by M. P. Starr, H. Stolp, H. G. Truper, R. A. Ballows, H. G. Shegel (The Prokaryotes—Vol. II Streptomycetacee—Springer Verlag Ed., 1981) demonstrates the absence of characteristic sugars; this confirms hence that SD18 belongs to the Streptomyces genus.

Like other microorganisms, Streptomyces SP. NCIB 12629 may undergo variations.

For example, artificial variants or mutants may be obtained by treatment with various known mutagens, as x-rays or U.V. light, high-frequency radiation and such chemical substances as nitrous acid, halogenated alkylamines, nitrosoguanidine, camphor, and the like.

All of the variants or mutants, both of natural origin or man-made, which belong to the Streptomyces species and produce AB-011 Antibiotics are regarded as equivalent to Streptomyces SP. NCIB 12629 strain and are included within the purview of the present invention.

Process of preparation of AB-011 Antibiotics

The process for the preparation of AB-011 Antibiotics consists in cultivating Streptomyces SP. NCIB 12629, or of an equivalent mutant thereof, under conditions of controlled aerobic fermentation in an aqueous nutrient medium, and in subsequently separating said antibiotics by means of per se known methods.

Nutrient culture media or fermentation broths may be used which are customarily used for the production of antibiotics; however, some culture media are preferred. The cultivation media should contain sources of carbon and nitrogen assimilable by the microorganisms of Streptomyces genus, and, furthermore, low levels of inorganic salts. They should furthermore contain traces of those metals, necessary for the growth and the development of the microorganisms, which may be already present as impurities in the sources of carbon or of proteinic nitrogen supplied for the bacterial growth, or, whenever necessary, these may be added to the culture medium.

As a carbon source, carbohydrates may be used which may be of the type of saccharides, such as, e.g., glucose or fructose, and of the type of starches, or of products similar to them from an industrial standpoint, such as, e.g., dextrin, soluble starch, or polyalcohols, such as, e.g., glycerol. Such compounds may be used either individually, or combined with one another.

The concentration of the source of carbon in the culture medium generally depends on the type and amount of the other ingredients contained in said medium; however, concentrations within the range of from 0.5 to 5% by weight are generally satisfactory.

As a nitrogen source, both proteinic extracts such as, e.g., yeast extract, casein hydrolysate, or peptone, and meals, such as, e.g., soybean meal, or industrial products available on the market for that purpose, such as, e.g., proflo, corn steep liquor or distillers, solubles may be used. These compounds may be used, both individually and combined with one another, at concentrations in the culture medium which may be within the range of from 0.1% to 4% by weight.

As the inorganic salts, there may be used, for example, sodium salts, potassium salts, magnesium salts, ammonium salts, calcium salts, such as phosphates, sulfates, chlorides, carbonates and nitrates.

The trace metals may be e.g., cobalt, manganese, iron and the like.

Some culture media display a special ability to stimulate the production of AB-011 Antibiotics by Streptomyces SP. NCIB 12629; among these, for example, the following aqueous formulations may be mentioned, which are used in the preparation examples set forth in the following:

| Ingredients | Concentration g/l |
|---|---|
| P-Culture Medium | |
| starch | 20 |
| glucose | 10 |
| calcium carbonate | 3 |
| casein hydrolysate | 2 |
| proflo (cotton seed flour) | 2 |
| meat extract | 2 |
| yeast extract | 2 |
| V-Culture Medium | |
| tryptone | 10 |
| meat and liver peptone | 10 |
| glucose | 5 |
| yeast extract | 5 |
| $K_2HPO_4$ | 1 |
| S Medium | |
| soluble starch | 10 |
| glucose | 5 |
| potassium nitrate | 2 |
| sodium chloride | 2 |
| monobasic potassium phosphate | 2 |
| hydrolyzed casein | 1 |
| calcium carbonate | 1 |
| magnesium sulfate heptahydrate | 0.5 |
| iron sulfate heptahydrate | 0.01 |

The strain of Streptomyces SP. NCIB 12629 may be grown at temperatures within the range of from 20° C. to 35° C., and preferably from 25° C. to 30° C.

The pH value generally may be within the range of from about 5 to about 9.

The sterile air which is injected into the culture medium is generally used in such amounts as to maintain in the medium an oxygen concentration equal to, or higher than, 20% of saturation value.

The production of the antibiotics during the fermentation may be monitored by tests of antibiotic activity on broth samples.

The fermentation is carried out for a time such as to obtain a substantial antibiotic activity; times of 72–120 hours are generally sufficient.

Separation and purification of the antibiotics

After the cultivation under the above fermentation conditions, AB-011 Antibiotics and the main components thereof: AB-011a and AB-011b Antibiotics, may be separated from the culture broth and subsequently purified by per se conventional methods in the art of fermentation. Such methods include, e.g., extraction with solvents, precipitation with non-solvents, ultrafiltration column chromatography, silicagel chromatography, cellulose chromatography, reverse-phase chromatography, chromatography on non-ionic macroporous resins, and the like.

The antibiotics produced during the fermentation may be found in the culture broth and/or in the mycelium mass.

A preferred method for recovering the AB-011 Antibiotics consists in filtering off the mycelium mass from the culture broth, subjecting the so-separated mycelium to an extraction with acetone or methanol, concentrating the extract under vacuum until the complete disappearance of the solvent, with an aqueous suspension being obtained which is combined with the culture broth.

The so-obtained solution containing the AB-011 is filtered through fiberglass-paper filters and is then percolated on a column of a non-ionic polystyrene resin, such as, e.g., of XAD-2 type (Rohm & Haas Co.), which adsorbs the AB-011 Antibiotics.

The resin is then washed with two volumes, referred to its bed, of water, and is then eluted with three volumes, still referred to its bed, of an 8:2 (V/V) mixture of acetone:water.

The fractions which contain the AB-011 Antibiotics, identified by means of biological tests of activity on Botrytis, are combined with one another and are then concentrated under vacuum to dryness in order to yield a raw product containing the AB-011 Antibiotics, substantially constituted by AB-011a Antibiotic and AB-011b Antibiotic.

Both pure AB-011a-Antibiotic and pure AB-011b Antibiotic are then isolated from the raw product by chromatography on reverse-phase, using a column packed with silica of MATREX silica C18 type (by Amicon Europe, Lausanne, Switzerland), with an eluent system formed by an "A" eluent consisting of water containing 25 millimols per liter of $KH_2PO_4$ and 7 millimols per liter of tetramethyl-ammonium chloride, and by a "B" eluent consisting of methanol, using a linear gradient of from 50% up to 80% of "B" eluent in "A" eluent.

The fractions which contain the AB-011a Antibiotic in a pure state and the AB-011b Antibiotic in a pure state are separately concentrated under vacuum until methanol completely disappears and, by cooling down the remaining aqueous solutions to 2° C., the precipitation of AB-011a and AB-011b Antibiotic—which are centrifuged off—is respectively obtained.

AB-011a and AB-011b Antibiotics, so separated from their respective solutions, are suspended in water and centrifuged again. After removing the supernatant solutions, and drying under vacuum at 40° C. for 2 hours, pure AB-011a Antibiotic and pure AB-011b Antibiotic are respectively obtained.

Biological activity

AB-011 Antibiotics, and the components thereof, i.e,. AB-011a Antibiotic and AB-011b Antibiotic, are endowed with antimicrobial activity, and especially antifungal activity.

Their antifungal activity turns out to be particularly high against phytopathogenic fungi which infest herbaceous, arboricultural, industrial and horticultural cultivations.

The antimicrobial activities, both in vitro and in vivo, of AB-011 Antibiotics were determined by means of the methods described below.

Tests for "in vitro" activity

The antimicrobial activity of AB-011 Antibiotics is determined by mean of the usual methods, by means of suitable dilution of a liquid growth medium.

In Table D below, the minimum inhibiting concentrations are reported.

For phytopathogenous fungi, the minimum concentration of AB-011 Antibiotics was determined which, under controlled conditions in agarized medium, causes a reduction in mycellar growth of 90% as referred to the control.

TABLE D

| Microorganism | Minimum concentrations of AB-011 Antibiotics (μg/ml) |
|---|---|
| Botrytis cinerea | 17 |
| Cercospora beticola | 100 |
| Cercosporella herptotrichoides | 30 |
| Colletotrichum coffeanum | 30 |
| Fusarium moniliforme | 30 |
| Fusarium roseum | 8 |
| Helminthosporium gramineum | 100 |
| Helminthosporium teres | 1.5 |
| Helminthosporium sativum | 3 |
| Piricularia oryzae | 25 |
| Pythium irregulare | 100 |
| Rhizoctonia solani | 20 |
| Sclerotium cepivorum | 3 |
| Septoria nodorum | 6 |
| Ustilago maydis | 20 |
| Candida albicans | 3.5 |
| Sarcina lutea | 0.3 |

Fungicidal activity "in vivo"

The fungicidal activity in vivo is measured by using the following method: B-011 Antibiotics in water-acetone solution at 20% V/V are sprinkled onto the lower blades of leaves of plants grown in pot inside a conditioned room.

One day later, an inoculum of the tested fungus is sprayed on the upper blade of the leaves of the plants, and these latter are kept under incubation conditions inside a conditioned room for about eight days.

At the end of said time, the seriousness of the infection is evaluated by means of scores of an evaluation scale ranging from 100 (=healthy plant) down to 0 (=completely infected plant).

The data relevant to the preventive activity in vivo is reported below in Table E.

Strictly analogous results of antifungal activity are obtained by using the individual antibiotics: AB-011a and AB-011b.

For the purposes of their practical use, both in agriculture and in other sectors of use, the antibiotics according to the present invention should be used as suitable compositions.

TABLE E

| Fungus | AB-011 Antibiotics concentration, g/l | Preventive activity |
|---|---|---|
| Plasmopara viticola | 0.5 | 100 |
|  | 0.125 | 100 |
|  | 0.06 | 100 |
| Sphaeroteca fuliginea | 0.5 | 85 |
|  | 0.125 | 40 |
|  | 0.06 | 0 |
| Botrytis cinerea | 0.5 | 100 |
|  | 0.125 | 70 |
|  | 0.06 | 15 |

These compositions contain, besides an antibiotic according to the present invention as their active principle, inert solid carriers (e.g., kaolin, silica, talc, attapulgite, diatomaceous earth, and so forth), or inert liquid carriers (organic solvents, vegetable or mineral oils, water and their mixtures), and possibly other additives which are normally used in the art of formulations, such as surfactants, suspending agents, dispersants and wetting agents.

In case of particular application requirements, or in order to expand the range of action of the compositions, other active ingredients, such as other insecticides, herbicides, fungicides or fertilizers may be added to such compositions.

The application doses vary as a function of different factors, such as the type and the degree of infestation, the type of composition used, climatic and environmental factors.

For practical uses in agriculture, doses of AB-011 Antibiotics within the range of from 10 to 500 g/ha yield satisfactory results.

EXAMPLES

The following are some examples supplied for the purpose of still further illustrating the invention, but without limiting it.

EXAMPLE 1

Fermentation of Streptomyces SP. NCIB 12629 strain

An ampoule containing 5 ml of the culture of Streptomyces SP. NCIB 12629 in the above-described "V" medium (stored in glycerol at 10% at −20° C.) is used in order to inoculate 150 ml of "V" medium; this latter is incubated for hours on a rotating shaker (150 rpm) at 28° C.

This culture is used to inoculate a fermenter (rated volume 10 liters) containing 7 liters of "S" medium, to which 0.01 g/l of Tween 2000 is added to act as an antifoaming agent, under the following conditions: temperature 29° C., air flowrate 120 liters/hour, stirring 320 rpm, fermentation time 96 hours.

The so-obtained fermentation broth is filtered through paper and the mycelium is separated.

For the subsequent operations of purification, a total volume of 28 liters, obtained from four fermentations carried out under the above disclosed conditions, is used.

Separation of AB-011 Antibiotics 28 liters of fermentation broth is filtered through a Whatman GF D fiberglass filter and the separated mycelium is extracted with acetone.

The acetonic extract is concentrated under vacuum until the total disappearance of the solvent and the residual aqueous solution is combined with the previously filtered broth.

The so-obtained solution is ultrafiltered through a GR-61 membrane (cut-off 20,000), until 3.2 liters remain of the retained fraction.

The retained fraction is then diluted to 25 liters with water, and is ultrafiltered again, under the same conditions, a volume of permeate of 20.5 liters being obtained. The second retained fraction, of 4.0 liters, turns out to be poorly active in the activity test, with the activity being computed by measuring the 8Botrytis growth inhibition halo over agar, and is discarded.

The first ultrafiltrate of 25 liters is concentrated on a GR-90 membrane (cut-off 2000), until 3.6 liters remain in the retained fraction, whilst the ultrafiltrate (21.0 liters) turns out to be poorly active on and is discarded. The retained fraction, on the contrary, contains 60% of the initial activity.

The second ultrafiltration permeate 20.5 liters) is concentrated on a GR 90 membrane (cut-off 2000) in the same way as above, and the residual 3.0 liters contain about 30% of the initial activity.

GR-61 and GR-90 membranes belong to the range traded by DDS-Nakskov (Denmark) and were used on a Lab-20 module, traded by the same company.

The two retained fractions (3.6 liters+3 0 liters) are combined with each other and are percolated on a column (diameter 45 mm; height of resin bed 30 cm) of non-ionic polystyrene resin XAD-2 (Rohm & Haas Co.), which adsorbs the AB-011 Antibiotics. During the percolation, an inlet flowrate of 100 ml/hour is maintained. The resin is subsequently washed with two volumes, referred to its bed, of water, and is then eluted with 3 volumes, still referred to its bed, of an 8:2 V/V acetone/water mixture.

The fractions which contain AB-011 Antibiotics, identified by means of biological tests carried out on Botrytis, are combined and are concentrated to dryness under vacuum, thus yielding a raw material containing AB-011 Antibiotic substantially constituted by AB-011a Antibiotic and AB-011b Antibiotic.

The raw product is collected with 300 ml of methanol, to which 300 ml of water is subsequently added. Pure AB-011a Antibiotic and pure AB-011b Antibiotic are then isolated from the raw material by reverse-phase chromatography, using a column filled with 350 g of silica, of MATREX Silica C18 type (Amicon Europe, Lausanne, Switzerland), with an eluent system formed by an "A" eluent constituted by water containing 25 mM monobasic potassium phosphate +7 mM tetramethyl-ammonium chloride, and by a "B" eluent containing methanol, using a gradient according to the following Table:

| Composition of the eluent system (AB-(V/V) | Volume of the eluent system ml |
|---|---|
| 1/1 | 500 |
| 45/55 | 150 |
| 40/60 | 150 |
| 35/65 | 150 |
| 30/70 | 150 |
| 25/75 | 150 |
| 20/80 | 2000 |

Pure AB-011a Antibiotic is collected as 320 ml inside the elution range between 3000 and 3320 ml, whilst AB-011b Antibiotic is collected as 700 ml inside the elution range between 3700 and 4400 ml.

The so-collected fractions are evaporated under vacuum up to total methanol disappearance, and then are left standing for 24 hours at 4° C. From these solutions, AB-011a Antibiotic and AB-011b Antibiotic respectively precipitate, and are collected by centrifugation. They are then suspended again in water and centrifuged.

After drying, 70 mg of AB-011a Antibiotic, as a light yellow-colored powder, and 20 mg of AB-011b Antibiotic as a deep yellow-colored powder are obtained.

The physical-chemical characteristics of the products have been reported above.

EXAMPLE 2

Fermentation of Streptomyces SP. NCIB 12629

A freeze-dried ampoule of Streptomyces SP. NCIB 12629 strain is opened under aseptic conditions, and is rehydrated with sterile distilled water. The suspension obtained is used in order to inoculate a 500 ml Erlenmeyer flask containing 100 ml of "P" culture medium, as described above, and is then incubated for 90 hours on a rotating shaker at 180 rpm at 28° C.

At the end of this time, the culture broth is centrifuged in order to separate it from the mycelium, and is used for the biological tests.

EXAMPLE 3

Fermentation of Streptomyces SP. NCIB 12629

A freeze-dried ampoule of Streptomyces SP. NCIB 12629 strain in rehydrated and used to inoculate the "P" culture medium, as described in Example 2.

The culture is incubated for 72 hours on a rotating shaker at 180 rpm at 28° C.

From the culture thus obtained, 5 ml are used to inoculate a 500 ml Erlenmeyer flask containing 100 ml of "S" culture medium (SCM), described above, which is then incubated for 120 hours on a rotating shaker at 180 rpm at 28° C.

At the end of this, the culture broth is treated and used in the biological tests according to Example 2.

EXAMPLE 4

Fermentation of Streptomyces SP. NCIB 12629

A 100 ml Erlenmeyer flask containing 25 ml of "P" culture medium (PMB), as described above, is inoculated with a portion of a colony of Streptomyces SP. NCIB 12629 strain, drawn under aseptic conditions from a slab or from a slant of agarized "P" medium.

This culture is then incubated for 72 hours on a rotating shaker at 180 rpm at 28° C. The incubated culture is then inoculated into a 100 ml Erlenmeyer flask containing 20 ml of the same "P" medium up to a concentration of 5% and the whole is incubated for 120 hours under the same conditions as in Example 2.

At the end of this time, the culture broth is treated in the safe way as in Example 2, and is sent to biological testing.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. AB-011a Antibiotic, which is a solid substance comprising:
   (a) a good solubility in dimethylsulfoxide and in (1:1 V/V) ethanol/water or (1:1 V/V) methanol/water blends poor solubility in water, rather good solubility in ethanol and methanol;
   (b) an approximate elemental analysis expressed as % values:
   carbon: 58.86;
   hydrogen: 7.64; and
   nitrogen: 1.11;
   (c) a molecular weight of about 1,197.65;
   (d) maximum absorbance peaks in U.V. light of:
   2.269 at 350.4 nm; 2.197 at 332.6 nm; 1.403 at 317.3 nm;
   0.679 at 303.3 nm; 0.118 at 381.1 nm; 0.097 at 405.6 nm, at a concentration of 0.029 mg/ml of methanol;
   (e) maximum absorbance peaks in infrared light at $(cm^{-1})$:
   3421, 2960, 2930, 2855, 2035, 1718, 1634, 1570, 1448, 1403, 1383, 1340, 1302, 1268, 1168, 1063, 1036, 1009, 989, 906, 848, 794, 575, 526, 473;
   (f) $^1$H N.M.R. spectrum, main peaks:
   δTMS (ppm): 6.54–6.1* (m, 8H); 5.92 (m, 1H); 5.69 (m, 1H); 5.41 (m, 2H); 5.15 (m, 1H); 4.92 (m, 1H); 4.77–4.22 (m, 6H); 4.22–3.45* (m, 8–10H); 3.37–3.07* (m, 6–7H); 3.02 (t, 1H); 2.93 (t, 1H); 2.88–2.72* (m, 3H); 2.45–2.27* (m, 3–4H); 2.27–2.05* (m, 3H); 2.05–1.85* (m, 3H); 1.85–1.66* (m, 1H); 1.66–1.15* (m, 30–33H); 1.10 (d, 3H); 0.99 (d, 3H); 0.90 (m, 6H);
   (g) $^{13}$C-N.M.R. spectrum, main peaks:
   δTMS (ppm): 208.6 (s); 176.3 (s); 170.3 (s); 135.8 (d); 134.6 (d); 133.5 (d); 133.2 (d); 132.9 (d); 132.7 (d); 131.7 (d); 131.4 (d); 130.0 (d); 129.5 (d); 100.3 (d); 99.8 (d); 97.4 (s); 97.3 (d); 87.1 (d); 84.4 (d); 79.9 (d); 75.0 (d); 73.5 (d); 73.1 (d); 72.1 (d); 70.7 (d); 70.0 (d); 69.0 (d); 67.1 (d); 66.1 (d); 65.9 (d); 64.0 (d); 58.1 (d); 56.9 (q); 56.3 (d); 51.6 (t); 50.5 (t) 44.7 (t); 43.0 (t); 42.5 (t); 39.7 (d); 39.4 (d); 39.0 (t); 37.5 (t); 36.3 (t); 34.4 (t); 32.1 (t); 31.7 (t); 29.3 (t); 18.0 (q); 17.9 (q); 17.1 (q); 16.0 (q); 11.5 (q);
   (h) $R_f$ values by thin-layer chromatography (TLC) on 60F 254 slab (Merck-Schuchardt);
   0.25 in ethanol:dioxane:aqueous solution of ammonia at 30%:water (8:1:1:1); 0.0 in 17:3 methylene chloride : methanol; $R_f$ values by reverse-phase chromatography on Merck-Schuchardt RP 18F-254 slab;
   0.29 in methanol : aqueous solution containing 25 mM monobasic potassium phosphate +7 mM tetramethyl-ammonium chloride (8:2);
   0.44 in methanol:acetonitrile:aqueous solution containing 25 mM monobasic potassium phosphate+7 mM tetramethyl-ammonium chloride (4:4:2);
   0.13 in methanol:10 mM aqueous solution of monobasic ammonium phosphate adjusted at pH 7.5 with phosphoric acid (8:2);
   0.44 in methanol:acetonitrile:10 mM aqueous solution of monobasic ammonium phosphate adjusted at pH 7.5 with phosphoric acid (4:4:2);
   (i) a retention time $(R_t)$ of about 7 minutes by reverse-phase HPLC on Hibar Li ChroCART Li-Chrosorb RP-18 column;
   Forecolumn: Guard Pak RCSS C 18;
   Eluent with methanol : acetonitrile: 25 mM aqueous solution of monobasic potassium phosphate +7 mM tetramethyl-ammonium chloride in water (4:4:2), with a flowrate of 0.8 ml/minute at 40° C.

2. AB-011b Antibiotic, which is a solid substance comprising:
   (a) maximum absorbance peaks in U.V. light of:
   2.872 at 349.9 nm; 2.747 at 332.4 nm; 1.999 at 316.9 nm; 0.987 at 303.3 nm; at a concentration of 0.04 mg/ml of methanol;
   b) approximate elemental analysis, determined on a sample left standing under vacuum at 40° C. for 2 hours, expressed as % values:
   carbon: 58.51;
   hydrogen: 8.14;
   nitrogen: 1.03;
   (c) maximum absorbance peaks in infrared light at $(cm^{-1})$:
   3415, 2926, 2855, 2060, 1721, 1634, 1568, 1450, 1406, 1383, 1302, 1264, 1190, 1168, 1063, 1036, 1007, 988, 906, 847, 804, 722, 664, 618, 576, 509, 471, 446;
   (d) molecular weight of about 1,181;
   (e) $^1$H-N.M.R. spectrum, main peaks:

δTMS (ppm): 6.45-6.05 (m, 8H); 5.93 (m, 1H); 5.70 (m, 1H); 5.40 (m, 2H); 5.13 (m, 1H); 4.73-4.30 (m, 6H); 4.27-3.45* (m, 8-9H); 3.37-3.09* (m, 6-7H); 3.02 (t, 1H); 2.94 (t, 1H), 2.75-2.60* (m, 1H); 2.44-2.28* (m, 3H); 2.28-1.81* (m, 7-8H); 1.81-1.47* (m, 5H); 1.47-1.16* (m, 30-33H); 1.1 (d, 3H); 0.99 (d, 3H); 0.91 (m, 6H);

(f) $^{13}$C-N.M.R. spectrum, main peaks:

δTMS (ppm): 208.7 (s); 176.3 (s); 174.9 (s); 170.4 (s); 135.7 (d); 134.7 (d); 133.5 (d); 133.3 (d); 132.9 (d); 132.7 (d); 131.7 (d); 131.5 (d); 130.0 (d); 129.5 (d); 103.3 (d); 100.0 (d); 97.4 (s); 96.9 (s); 87.2 (d); 84.5 (d); 80.0 (d); 75.1 (d); 74.9 (d); 73.1 (d); 72.2 (d); 70.7 (d); 70.0 (d); 69.0 (d); 68.5 (d); 67.8 (d); 67.1 (d); 65.9 (d); 65.7 (d); 63.9 (d); 58.1 (d); 56.9 (q); 56.2 (d); 51.5 (t); 50.7 (t); 46.5 (t); 44.7 (t); 42.5 (t); 39.1 (t); 38.5 (t); 38.0 (t); 36.3 (t); 34.1 (t); 32.3 (t); 31.8 (t); 31.6 (t); 29.3 (t); 18.1 (q); 18.0 (q); 17.9 (q); 17.4 (q); 16.3 (q); 11.6 (q).

$R_f$ values by thin layer chromatography (TLC) on 60 F 254 slab (Merck-Schuchardt):

0.32 in ethanol:dioxane:aqueous solution of ammonia at 30% : water (8:1:1:1);

0.00 in 17:3 methylene chloride:methanol;

$R_f$ values by reverse-phase chromatography on Merck-Schuchardt RP 18F-254 slab;

0.22 in methanol : aqueous solution containing 25 mM monobasic potassium phosphate +7 mM tetramethyl ammonium chloride (8:2);

0.35 in methanol:acetonitrile:aqueous solution containing 25 mM monobasic potassium phosphate +7 mM tetramethyl-ammonium chloride (4:4:2);

0.08 in methanol:10 mM aqueous solution of monobasic ammonium phosphate adjusted at pH 7.5 with phosphoric acid (8:2);

0.20 in methanol:acetonitrile:10 mM aqueous solution of monobasic ammonium phosphate adjusted at pH 7.5 with phosphoric acid (4:4:2);

(h)

Retention time ($R_t$) of about 9 minutes by reverse-phase HPLC on Hibar Li ChroCART Li-Chrosorb RP-18 column;

Forecolumn: Guard Pak RCSS C 18, eluting with methanol:acetonitrile:25 mM aqueous solution of monobasic potassium phosphate +7 mM tetramethyl-ammonium chloride (4:4:2), with a flowrate of 0.8 ml/minute at 40° C.

3. AB-011 Antibiotics obtained by the controlled cultivation under aerobic conditions of Streptomyces SP. NCIB 12629, or of an equivalent mutant thereof, in an aqueous nutrient cultivation medium, containing sources of carbon, nitrogen and inorganic salts, which are substantially constituted by AB-011a Antibiotic and AB-011b Antibiotic, as defined in claims 1 and 2.

4. Process for the preparation of AB-011 Antibiotics comprising the cultivation of Streptomyces SP. NCIB 12629, or of an equivalent mutant thereof, under conditions of controlled aerobial fermentation in an aqueous nutrient medium containing assimilable sources of carbon, nitrogen and inorganic salts, until a substantial antibiotic activity is obtained, subsequently recovering said antibiotics by means of known methods.

5. Process according to claim 4, wherein the fermentation is carried out at temperatures within the range of from 25° C. to 30° C.

6. Process according to claim 4, wherein the fermentation is carried out at a pH within the range of from 5 to 9.

7. Process according to claim 4, wherein the AB-011 Antibiotics are isolated from the fermentation broth by filtration and subsequently by chromatographic techniques.

8. The process according to claim 4, further comprising separating main components designated as AB-011a Antibiotic and AB-011b Antibiotic.

9. Process according to claim 8, wherein AB-011a Antibiotic and AB-011b Antibiotic are isolated by reverse-phase chromatography on a silica gel column using in the elution a linear gradient of from 50% to 80% of methanol in the mixture constituted by water containing 25 mM/l of $KH_2PO_4$ and 7 mM/l of $(CH_3)_4NCl$.

10. A biologically pure culture of Streptomyces SP. NCIB 12629 microorganism or of an equivalent mutant thereof, capable of producing AB-011 Antibiotics in isolatable amounts by the controlled aerobic fermentation in an aqueous nutrient medium comprising assimilable sources of carbon, nitrogen and inorganic salts.

11. Method of controlling fungus infections of plants comprising treating either said plants of the growing area immediately adjacent thereto with a fungicidally effective amount of a compound selected from the class consisting of AB-011 Antibiotics, AB-011a Antibiotic and AB-011b Antibiotic as a fungicide.

12. Fungicidal compositions comprising as their active ingredient a compound selected from the class consisting of AB-011 Antibiotics, AB-011a Antibiotic and AB-011b Antibiotic, together with inert solid or liquid carriers.

* * * * *